United States Patent [19]

Engel et al.

[11] Patent Number: 5,446,033

[45] Date of Patent: Aug. 29, 1995

[54] STABILIZED HEXADECYLPHOSPHOCHOLINE SOLUTIONS IN GLYCEROL ALKYL ETHERS

[75] Inventors: Jürgen Engel, Alzenau; Elisabeth Wolf-Heuss, Mosbach; Helmut Orth, Hanau; Burkhard Wichert, Bielefeld; Dieter Sauerbier, Werther, all of Germany

[73] Assignee: Asta Medica AG, Germany

[21] Appl. No.: 137,964

[22] Filed: Oct. 19, 1993

[30] Foreign Application Priority Data

Oct. 23, 1992 [DE] Germany .................. 42 35 911.2

[51] Int. Cl.⁶ .......................................... A61K 31/685
[52] U.S. Cl. ................................. 514/77; 514/723; 514/709; 514/784
[58] Field of Search ................. 514/77, 715, 784, 769; 568/581

[56] References Cited

U.S. PATENT DOCUMENTS

| | | | |
|---|---|---|---|
| 4,837,023 | 6/1989 | Eibl | 424/439 |
| 5,008,294 | 4/1991 | Jordon | 514/731 |
| 5,049,552 | 9/1991 | Eibl | 514/77 |
| 5,153,179 | 10/1992 | Eibl | 514/34 |

FOREIGN PATENT DOCUMENTS

| | | |
|---|---|---|
| 0225608 | 12/1986 | European Pat. Off. . |
| 0419998 | 9/1990 | European Pat. Off. . |
| 3343530 | 6/1985 | Germany . |

OTHER PUBLICATIONS

Kirk-Othmer 'Encyclopedia of Chemical Technology', Third Edition vol. 6, John Wiley & Sons, 1979.
German Office Action, May 17, 1993.
Derwent Abstract, 1992.

*Primary Examiner*—C. Warren Ivy
*Assistant Examiner*—Evelyn Huang
*Attorney, Agent, or Firm*—Cushman Darby & Cushman

[57] ABSTRACT

Solutions of alkylphosphocholines in glycerol alkyl ethers having enhanced storage stability containing a buffer which maintains the pH value to a range between 4 and 6.

11 Claims, No Drawings

STABILIZED HEXADECYLPHOSPHOCHOLINE SOLUTIONS IN GLYCEROL ALKYL ETHERS

The present invention relates to a pharmaceutical composition having increased stability.

BACKGROUND OF THE INVENTION

Alkylphosphoric acid compounds are known substances with anti-tumor effects.

German published patent 33 43 530.8 (U.S. Pat. No. 5,153,179) discloses preparations for administering pharmaceutically-active compounds including, e.g., phosphatidylcholine. This patent describes the use of aqueous compositions of those active ingredients and others and describes increased penetration of the blood-brain barrier and other tissue barriers, achieved through the use of glycerol alkyl ether as solvents for these active substances.

Investigation of the use of alkyl glycerols with alkyl phosphoric acids such as hexadecylphosphocholine led to the discovery of storage instability. That is, oxidative processes caused peroxides to be formed in the solution which later led to acids and hence a drop in pH due to further decomposition. The pH value is set at 4–6 in the specification.

SUMMARY OF THE INVENTION

In accordance with the present invention, the stability of solutions of hexadecylphosphocholine and related compounds in glycerol alkyl ethers has been increased through the use of a buffer. In particular a buffer is used which maintains the pH in the range 4 to 6.

It has, for example, been found desirable, for topical administration of hexadecylphosphocholine, to use the active substance together with at least one alkyl glycerol which contains 2–12 carbon atoms in the alkyl radical. The active substance may be attached to an ether group bound to one of the primary or secondary OH groups of the glycerol. Alkyl glycerols of this type enhance the effect of alkylphosphoric acid compounds. Preference is given to alkyl glycerols which contain 3–9 carbon atoms used alone or in mixtures. Particularly favorable effects are therefore displayed by a medication containing a) one or several alkylphosphoric acid compounds of the following General Formula I:

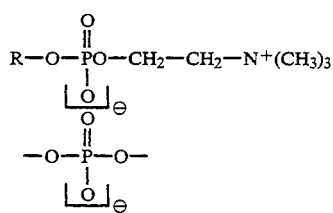

in which

R represents an alkyl group with 12–20 carbon atoms which may optionally contain a double bond or a triple bond b) an alkyl glycerol of the following General Formula II

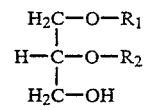

in which one of the radicals $R_1$ and $R_2$ represents an alkyl group with 2 to 12 carbon atoms and the other radical represents a hydrogen atom, as well as optionally additional conventional additives and diluents.

It is, for example, possible to consider a mixture of water and an alkyl glycerol mixture of nonyl or octyl glycerol, hexyl or pentyl glycerol and propyl or ethyl glycerol. An appropriate formulation for topical application contains for example 1–100 mg alkylphosphoric acid compound per ml alkyl glycerol or a corresponding alkyl glycerol mixture with water.

A mixture of this type is hereinafter also referred to as a cascade.

Alkyl glycerol-water mixtures containing, for example, nonyl glycerol, hexyl glycerol, propyl glycerol are preferred. Such mixtures preferably contain 3 of the glycerol ethers mentioned, namely a lower one (propyl), a medium one (hexyl) and a higher one (nonyl), the amount by weight of the lower ether being approximately as much as the sum of the amounts by weight of the two other glycerol ethers. The amount of water is about the same as the amount of the lower glycerol ether and is for example half the total amount of the glycerol ethers present.

Examples of this type of glycerol ether/water mixtures are listed below:

| | Water | Glycerol propyl ether | Glycerol hexyl ether | Glycerol nonyl ether |
|---|---|---|---|---|
| Parts by weight | 2 | 2 | 1 | 1 |

| | | Glycerol ethyl ether | Glycerol pentyl ether | Glycerol octyl ether |
|---|---|---|---|---|
| Parts by weight | | 2 | 2 | 1 | 1 |

A particular favorable carrier mixture for the alkylphosphoric acid compound hexadecylphosphochloline consists of a mixture of about 4 parts by weight of water, 4 parts by weight of propyl glycerol and 2 parts by weight each of hexyl glycerol and nonyl glycerol.

It is not necessary to add preservatives to solutions of this type, since microbiological load tests showed these solutions to have optimum antiseptic properties.

A 6% hexadecylphosphocholine solutions is for example compounded as follows:

| hexadecylphosphocholine | 0.600 g |
|---|---|
| glycerol-1-n-propyl ether | 3.145 9 |
| glycerol-1-n-hexyl ether | 1.570 g |
| glycerol-1-n-nonyl ether | 1.570 g |
| water | 3.145 g |
| | 10.030 g = 10 ml |

As noted above, it was found during stability storage that oxidative processes cause peroxides to be formed in the solution which later led to acids and hence a drop in pH due to further decomposition. This is shown in the following data:

| pH and peroxide number of a 6% hexadecylphosphocholine solution (untreated) | | | | | |
|---|---|---|---|---|---|
| | −4° C. | +2° C. | RT[1] | 31° C. | 41° C. |
| Initial Investigation | | | | | |
| pH value | | | 5.6 | | |
| peroxide value | | | 0.4 | | |
| 3 months | | | | | |
| pH value | 5.0 | 5.0 | 4.0 | 3.6 | 3.3 |
| peroxide value | 0.81 | 0.95 | 0.91 | 3.6 | 6.0 |
| 6 months | | | | | |
| pH value | 7.4 | 6.0 | 3.8 | 3.5 | 3.1 |
| peroxide value | 0.55 | 0.18 | 1.9 | 4.9 | 7.8 |

[1]Room Temperature

Attempts were made to control peroxide formation in hexadecylphosphocholine cascade solutions by gassing with nitrogen and covering with nitrogen after dispensing into 10 ml bottles. An attempt was also made to prevent peroxide formation by adding antioxidants. The results are shown below.

| pH and peroxide number in a 6% hexadecylphosphocholine solution in cascade (after gassing with nitrogen) | | | | | |
|---|---|---|---|---|---|
| | −4° C. | +2° C. | RT[1] | 31° C. | 41° C. |
| Initial Investigation | | | | | |
| pH value | | | 4.6 | | |
| peroxide number | | | 0.0 | | |
| 3 months | | | | | |
| pH value | 4.6 | 5.0 | 4.2 | 3.9 | 3.6 |
| peroxide number | 0.1 | 0.11 | 0.97 | 0.94 | 5.1 |
| 6 months | | | | | |
| pH value | 4.5 | 4.4 | 4.1 | 3.9 | 3.5 |
| peroxide number | 0.0 | 0.0 | 1.73 | 1.1 | 4.6 |

[1]Room Temperature

As can be seen from this data, the pH value falls and the peroxide content rises, notwithstanding the use of a nitrogen atmosphere.

The addition of antioxidants also did not improve the stability of the solutions, as shown in the following experimental data.

| pH value of hexadecylphosphocholine cascade with addition of antioxidants | | | | | |
|---|---|---|---|---|---|
| | −4° C. | +2° C. | RT[1] | 31° C. | 41° C. |
| With 0.1% sodium disulfite | | | | | |
| Initial pH value | | | 3.8 | | |
| 3-month pH value | 3.8 | 3.7 | 3.3 | 3.1 | 2.8 |
| With 0.01% ascorbyl palmitate and 0.05% alpha-tocopherol | | | | | |
| Initial pH value | | | 3.8 | | |
| 3-month value | 3.8 | 3.7 | 3.3 | 3.1 | 2.8 |

[1]Room Temperature

Thus, experiments have confirmed that the conventional formulation is not storage stable, and that the use of conventional agents to suppress peroxide formation, such as gassing with nitrogen to remove the oxygen from the solution and the addition of antioxidants, did not lead to storage stable solutions.

In accordance with the present invention, however, it was found that when, for example, a citrate buffer system was added in addition to the antioxidant sodium disulfite, the pH value could be maintained within the specification. The results are given below:

| pH value of hexadecylphosphocholine cascade solutions with added 0.1% sodium disulfite and citrate buffer (0.1 molar in the water phase) | | | | | |
|---|---|---|---|---|---|
| | −4° C. | +2° C. | RT[1] | 31° C. | 41° C. |
| Initial pH value | | | 5.6 | | |
| 3-month pH value | 5.6 | 5.6 | 5.3 | 5.1 | 5.2 |

[1]Room Temperature

Since sodium disulfide itself did not provide any beneficial effect as an antioxidant, a hexadecylphosphocholine cascade solution was prepared containing only citrate buffer to reduce the peroxide formation. It was surprisingly found that the addition of buffer was itself capable of suppressing the peroxide formation and thus preventing a decrease in the pH value.

| Hexadecylphosphocholine cascade solution with citrate buffer | | | | | |
|---|---|---|---|---|---|
| | −4° C. | +2° C. | RT[1] | 31° C. | 41° C. |
| Initial pH value | | | 5.8 | | |
| peroxide number | | | 0.58 | | |
| 3-month pH value | 5.8 | 5.8 | 5.8 | 5.8 | 5.7 |
| peroxide number | 0.33 | 0.29 | 0.41 | 0.51 | 0.58 |
| 6-month pH value | 5.8 | 5.8 | 5.8 | 5.7 | 5.6 |
| peroxide number | 0.02 | 0.39 | 0.11 | 0.36 | 0.54 |
| 12 months pH value | 5.8 | 5.8 | 5.7 | 5.6 | 5.3 |
| peroxide number | 0.06 | 0.04 | 0.18 | 0.11 | 0.4 |

[1]Room Temperature

The composition of 10 ml of a 6% buffered hexadecylphosphocholine cascade is as follows:

| | |
|---|---|
| hexadecylphosphocholine | 0.6000 g |
| D,L-glycerol-1-n-propyl ether | 3.1600 g |
| D,L-glycerol-1-n-hexyl ether | 1.5800 g |
| D,L-glycerol-1-n-nonyl ether | 1.5800 g |
| citric acid anhydrous | 0.0484 g |
| sodium hydroxide | 0.0227 g |
| purified water | 3.0889 g |
| | 10.0800 g = 10 ml |

The following mixtures are also suitable buffer mixtures: mixtures of disodium hydrogen phosphate/citric acid, succinic acid/sodium hydroxide, potassium dihydrogen phosphate/disodiumhydrogen phosphate sodium hydrogen maleate/sodium hydroxide, trismaleate/sodium hydroxide, potassiumdihydrogen phosphate/sodium hydroxide.

A mixture of citric acid and sodium hydroxide of pH value 5.3 is particularly preferred.

DETAILED DESCRIPTION OF PREFERRED EMBODIMENTS

The following example illustrates the invention.

EXAMPLE 1

Buffered 6% (W/V) hexadecylphosphocholine solution for topical application

Hexadecylphosphocholine solution is prepared by dissolving hexadecylphosphocholine in a buffered solvent called a cascade. 6.27 kg DL-glycerol-1-ethyl ether, 3.135 kg DL-glycerol-1-n-pentyl ether and 3.135 kg DL-glycerol-1-n-octyl ether were mixed and 1.19 kg hexadecylphosphocholine dissolved in this mixture.

Preparation of citrate buffer pH 5.3

0.0965 kg citric acid anhydrous are dissolved in 5.8 kg purified water and 0.047 sodium hydroxide in 0.3 kg purified water. The sodium hydroxide solution is then added to the citric acid solution until a pH value of 5.3 is reached. Water is then added to make up to 6.27 kg. 6.27 kg citrate buffer are then mixed with 13.73 kg solution of the hexadecylphosphocholine in the ether mixture. A uniform solution is obtained with nitrogen gassing. The solution is filtered through a membrane filter, pore size 0.2 μm, dispensed in 10 ml portions into brown dropper bottles and closed with pipette and protective cap.

What is claimed is:

1. An aqueous solution of at least one alkylphosphocholine having the formula:

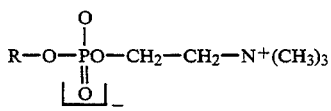

in which R is an alkyl group containing 12-20 carbon atoms which may contain a double or triple bond and at least one glycerol ether having the formula:

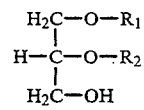

in which one of the groups $R_1$ and $R_2$ is an alkyl group containing 2 to 12 carbon atoms and the other of the groups $R_1$ and $R_2$ is hydrogen, said solution containing a buffer which maintains the pH in the range 4 and 6.

2. A solution according to claim 1 in which the buffer solution is a solution of citric acid and sodium hydroxide in water.

3. A solution according to claim 2 in which the buffer maintains the pH at 5.3.

4. A solution as set forth in claim 1 in which said alkylphosphocholine is hexadecylphosphocholine.

5. A solution as set forth in claim 1 in which said at least one glycerol ether is a mixture of glycerol ethers.

6. A solution as set forth in claim 1 in which said at least one glycerol ether is a mixture of a lower glycerol ether, a higher glycerol ether and a still higher glycerol ether.

7. A solution as set forth in claim 6 in which said lower glycerol ether is propyl glycerol, said higher glycerol ether is hexyl glycerol and said still higher glycerol ether is nonyl glycerol.

8. A solution as set forth in claim 7 in which there is about as much propyl glycerol by weight as the sum of the amounts of hexyl and nonyl glycerols by weight.

9. A solution as set forth in claim 7 in which the amount of water is about one-half the total amount of glycerol ethers.

10. A solution as set forth in claim 1 in which the amount of said at least one alkylphosphocholine is 1-100 mg per ml of said at least one glycerol ether.

11. A method of treating a tumor disease which comprises administering an effective amount of a solution according to claim 1.

* * * * *